Figure 1:
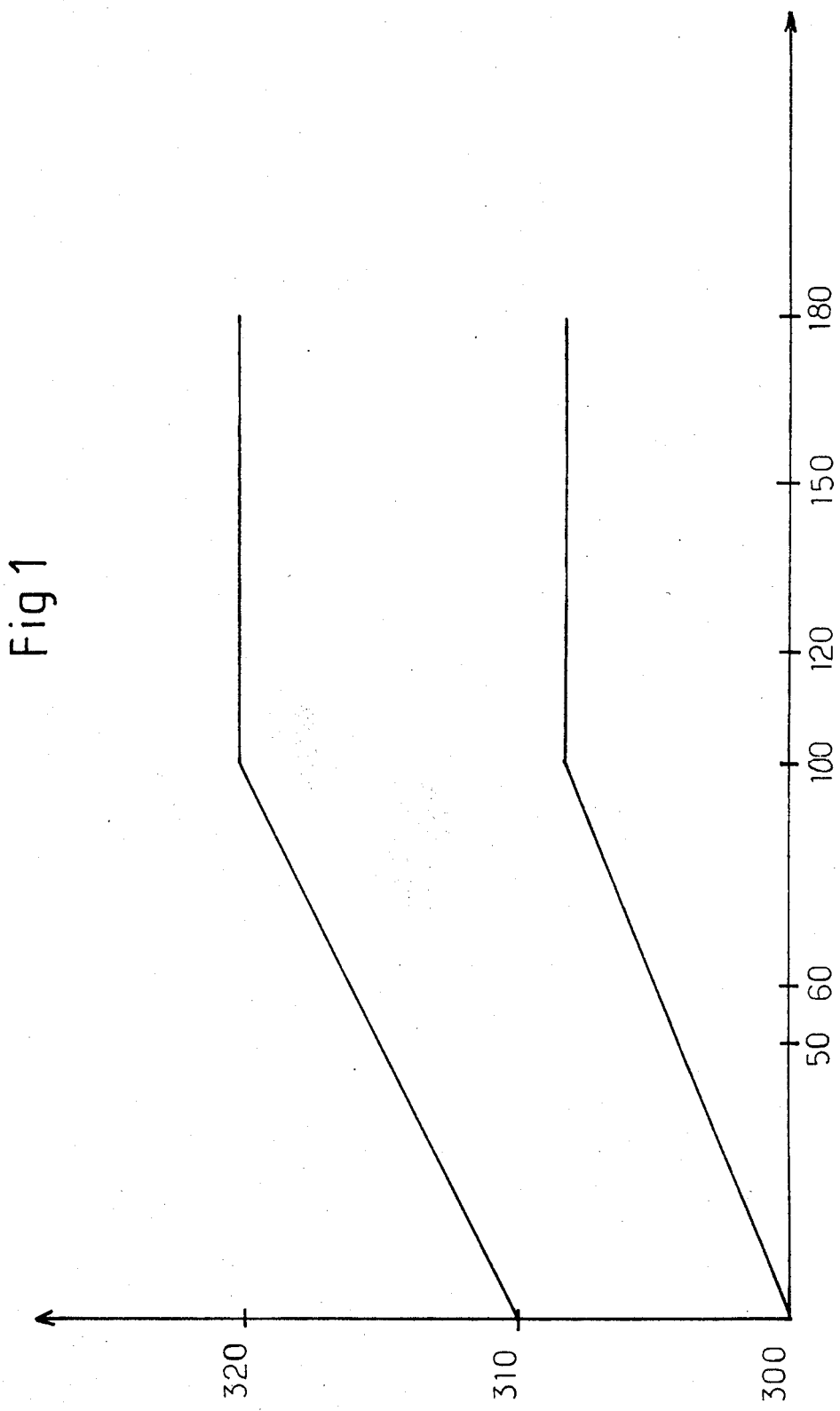

United States Patent [19]

Clarisse et al.

[11] Patent Number: 4,649,195

[45] Date of Patent: Mar. 10, 1987

[54] PROCESS FOR THE PREPARATION OF METAL DIPHTHALOCYANINES

[76] Inventors: Christian Clarisse, 7 Avenue de Normandie, 22300 Lannion; Marie-Thérèse Riou née Meston, 8 rue Etienne d'Orves, 22700 Perros Guirec; Marcel Auregan, 3 rue Charles Colvez, 22300 Lannion, all of France

[21] Appl. No.: 693,863

[22] Filed: Jan. 23, 1985

[30] Foreign Application Priority Data

Jan. 24, 1984 [FR] France ................. 84 01164

[51] Int. Cl.$^4$ ............................. C09B 47/067
[52] U.S. Cl. ..................................... 540/143
[58] Field of Search ................ 260/245.86, 245.89

[56] References Cited

FOREIGN PATENT DOCUMENTS 32256 12/1980 European Pat. Off. .
799901 12/1935 France .

OTHER PUBLICATIONS

Shklover et al, Chemical Abstracts, vol. 68, (1968), 78403g.
Moskalev et al, Chemical Abstracts, vol. 72, (1970), 742106.

*Primary Examiner*—Richard L. Raymond
*Attorney, Agent, or Firm*—Blakely, Sokoloff, Taylor & Zafman

[57] ABSTRACT

The present invention relates to a process for the preparation of lanthanide or yttrium diphthalocyanine, in which:
(a) a mixture of lanthanide or yttrium derivative and phthalonitrile is heated, the reaction temperature being kept below the critical temperature of endothermicity, then
(b) when an exothermicity appears the temperature is kept at a temperature below the decomposition temperature of the reactants,
(c) the lanthanide or yttrium diphthalocyanine obtained is recovered.

The products obtained may be used as electroactive agents.

8 Claims, 1 Drawing Figure

PROCESS FOR THE PREPARATION OF METAL DIPHTHALOCYANINES

The present invention relates to a process for the preparation of a metal diphthalocyanine which can be employed in particular as an electrochromic component.

Diphthalocyanines of di- or trivalent metals such as yttrium or the lanthanides are known to exhibit electrochromic properties.

A compound is said to exhibit electrochromic properties when this compound is liable to change color when the characteristics of the electric potential which is applied to it are modified.

Lutetium diphthalocyanine, which is by far the most widely studied compound in this field, can, when subjected to changes in potential in a suitable electrolysis cell, assume any oxidation state between $(-2)$ and $(+2)$, corresponding to the following colors: violet $(-2)$, blue $(-1)$, green $(0)$, yellow $(+1)$, and red $(+2)$.

Naturally, the advantage of this type of compound in colored visualizing and display devices can be imagined.

Although numerous processes for preparing these compounds have been proposed, experience shows that it is impossible to obtain, in particular from the laboratories for organic synthesis of diphthalocyanines, lutetium diphthalocyanine which is sufficiently pure to be employed directly without preliminary physical purification such as sublimation, the products delivered always having variable colors and properties depending on the batches.

The disparity in the properties of these products originates in the synthesis processes employed, which result in the formation of numerous by-products. The presence of these by-products requires the use of highly complex purification methods including successive extractions, fractional sublimation or chromatography. These analytical methods are not suitable for the preparation of lutetium diphthalocyanine in large quantities. It is therefore preferable to obtain a pure product immediately on completing the synthesis, which can be used directly for producing electrochromic devices, which is the aim of the present invention.

Furthermore, the processes of the prior art afford very low yields, which is particularly inconvenient, given the high cost of the starting materials.

In the prior art, the majority of the syntheses proposed for metal diphthalocyanines consist in heating a derivative of the metal in question with a phthalonitrile or with free phthalocyanine.

Such processes are described particularly in the paper by P. N. Moskalev and I. S. Kirin (Russian Journal of Inorganic Chemistry 15, 1, 1970), in the paper by A. G. Mac Kay et al. (Aust. J. Chem., 1974, 27, 955-64) or in British Pat. No. 2,063,903.

In the two papers mentioned above, it is found that, although much attention has been given to the characteristics and the structures of the products prepared, the processes employed for the synthesis of these compounds contain little detail; in any case, they result in highly complex mixtures, the electrochromic properties of which are sometimes very difficult to demonstrate.

It should be noted that the processes of the prior art consist substantially, after the starting materials have been mixed, in heating the mixture and, after heating times which are very variable or indeterminate, according to the authors, in removing the reaction mixture and attempting to extract the required compound therefrom.

The present invention relies on a fine analysis of the reaction and on the demonstration of the existence of two distinct stages in the synthesis of metal diphthalocyanines.

In fact, it appears that the synthesis of diphthalocyanines from phthalonitrile begins with an endothermic stage during which it is absolutely necessary to keep the temperature of the reaction medium below a maximum temperature which will be hereafter referred to as "critical temperature of endothermicity".

During this first stage there is formed, substantially though not exclusively, an intermediate compound which is indispensable in the synthesis of lutetium diphthalocyanine, probably a substituted or unsubstituted monophthalocyanine.

When this endothermic stage is completely finished, a temperature rise takes place, which corresponds to a second, exothermic stage. This exothermic reaction begins slowly during the first stage, but is masked by the endothermic reaction which is much more prominent. In this second stage as well, the reaction temperature should be kept below a maximum temperature which corresponds to the decomposition temperature of the starting materials and of the products formed.

This second stage corresponds to the formation of the metal diphthalocyanine as such. The metal diphthalocyanine formed is green in color.

For this reason, the present invention relates to a process for the preparation of lanthanide diphthalocyanine, in which:

(a) a mixture of a lanthanide derivative and phthalonitrile is heated, the reaction temperature being kept below the critical temperature of endothermicity, then (b) when an exothermicity appears, the temperature is kept at a temperature below the decomposition temperature of the reactants, in particular of the starting materials and products formed.

It should be noted that the term lanthanide employed in the present description can denote not only true lanthanides (from lanthanum to lutetium) but also the associated metals such as yttrium, the electron characteristics of which are similar to those of the lanthanides.

Among the lanthanide derivatives which can be employed, particular mention should be made of the organic derivatives of lanthanides, particularly acetates.

As mentioned earlier, the critical temperature of endothermicity is a function of the starting materials employed and, in the case of lutetium in the form of acetate, this critical temperature of endothermicity is 305° C.; where the second decomposition temperature is concerned, tnis is, of course, a function of the starting materials as well; in the case of lutetium acetate, this decomposition temperature is of the order of 320° C.

More precisely, in the case of lutetium the temperature in the first stage will preferably be between 290° C. and 305° C. The duration of this stage depends on the reaction temperature; the end of the reaction is marked by the appearance of an exothermic reaction characteristic of the formation of the diphthalocyanine. The temperature in the second stage is preferably between 305° C. and 305° C. to avoid extensive formation of lutetium monophthalocyanine, blue in color. Here again, the duration of this stage depends more particularly on the reaction temperature.

As an example, it is possible to indicate an advantageous temperature profile which corresponds to the reaction of lutetium acetate with ortho-phthalonitrile (in a ratio of 1/10 moles);

(a) target temperature varying linearly from 300° to 308° C. over 100 min;

(b) target temperature constant at 308° C. for 100 min.

As described here, the description given is essentially that of the preparation of lutetium diphthalocyanine, which is the compound of greatest interest, but it is certain that this process can readily be adapted to other rare earths which are also of interest, such as Gd, Tb, Dy, Ho, Er, Tm and Yb, in the case of which the temperatures of formation of the diphthalocyanines do not cover the range of the critical temperatures.

In the case of the other rare earths, difficulties may be encountered in certain cases in implementing the second reaction stage because critical temperatures may readily be reached, at which temperatures the exothermic synthesis reaction is not moderated. This is accompanied by a reduction in yield and results in the formation of free phthalocyanine.

The reaction is preferably carried out at atmospheric pressure, for example in an open reactor.

It is advantageous to operate using a gas stream, in particular a stream of an inert gas such as argon; in fact, this stream promotes the removal of the acetic acid formed, shifting the reaction equilibrium towards the formation of the required product.

Naturally, the starting materials must be as pure as possible; thus, ortho-diphthalonitrile should be recrystallized twice, and the lanthanide derivative should be synthesized as pure as possible.

In addition, it is important to keep the reaction medium agitated so as to operate in a homogeneous phase because, in the molten state, the densities of the reaction components are very different. This agitation also improves the release of the acetic acid formed.

The molar proportion of the compounds employed is preferably between 1/6 and 1/12, metal derivative/phthalonitrile, preferably 1/10. In principle, an excess of phthalonitrile (cheaper than the metal derivative) is employed to drive the reaction, but this rapidly results in the formation of free phthalocyanine, and for this reason it is undesirable to employ a molar excess of phthalonitrile which is too large.

The results noted during the use of the process according to the present invention have made it possible to demonstrate two considerable advantages of the present invention, namely:

a considerable simplification in the purification techniques, and a yield which is considerably increased relative to the yields observed during the use of previous techniques.

In fact, by virtue of a simple washing of the crude product with methanol and with dimethylformamide, pure lutetium diphthalocyanine is obtained with a yield of approximately 60%, while in the prior art the yields of pure product are much lower, and the content of undesirable free phthalocyanine is greater than that obtained in the use of the present invention.

The free phthalocyanine content of the product obtained is sufficiently low for the latter to be capable of being used directly after simple washing.

This improvement in the yields of the diphthalocyanine synthesis is of considerable importance in view of the price of the materials employed since, in fact, the lutetium acetate employed as starting material costs approximately 150,000 French francs per kg (1983).

The following examples are intended to demonstrate other advantages and features of the process as claimed in the present invention.

EXAMPLE 1

Synthesis of lutetium diphthalocyanine

Approximately 2 g of anhydrous lutetium acetate and twice-recrystallized phthalonitrile are mixed in a mortar in the molar proportion of 1 mole of lutetium acetate per 10 moles of phthalonitrile.

This mixture is put into an open tube placed vertically in a furnace and is continuously stirred. The temperature of the mixture is raised to 304° C. for approximately 1 h 30 min; then, when the temperature rises, it is maintained at 312° C., and this temperature is maintained for approximately 1 h 30 min.

The tube is then taken out and cooled in open air. The black, brittle product formed at the bottom of the tube is collected and ground in a mortar.

This product is washed three times with high purity methanol, each washing involving two operations, namely ultrasonic agitation followed by centrifuging to separate the two phases. The product is then subjected to three washings with dimethylformamide using the same procedure.

Finally, this is completed by two methanol rinses with drying at 100° C.

After being dried, the product obtained is characterized by infrared and UV-visible spectroscopy.

It is found that the percentage of free phthalocyanine, determined by infrared spectroscopy and calculated relative to the diphthalocyanine, is below 5%, while it is several tens % in the products obtained by the processes of the prior art.

EXAMPLE 2

This example made it possible to demonstrate the importance of the critical temperature of endothermicity, which is 305° C. for lutetium acetate.

Comparative tests were therefore carried out under the conditions of Example 1, but employing the 2 target temperature profiles shown in the attached FIGURE.

In a first experiment the control set point was varied linearly from 300° C. to 308° C. during the exothermic period.

In this case the temperature profile conforms to that of the process as claimed in the present invention.

In a second series of experiments, the temperature set point was varied from 310° C. to 320° C. (that is to say above the critical temperature of endothermicity) over 100 min and it was then kept at 320° C. for 100 min.

In both cases, the products obtained were washed in the same manner with the same solvents.

These products were characterized and the results are given in the attached Table.

TABLE

|  | 1st example | 2nd example |
|---|---|---|
| Solubility in dichloromethane | green color soluble (40 mg/100 ml) green solution | blue color poorly soluble ≦10 mg/100 ml blue solution |
| UV-visible spectrum | 659 nm | 627 nm |
| Infrared spectrum | 1,451 cm$^{-1}$ 1,322 cm$^{-1}$ | 1,332 cm$^{-1}$ 1,074 cm$^{-1}$ 1,063 cm$^{-1}$ |
| Electrochemistry | Perfectly revers- | No reversibility |

TABLE-continued

|  | 1st example | 2nd example |
|---|---|---|
| in solution (cyclic voltammetry) | ible reaction producing the various above mentioned colors | |
| Sublimation | Sublimes from 460° without decomposition - green film | Does not sublime at all |

By inspecting this Table, it is found that a simple variation of 10° in the reaction temperature profile results in two completely different products. In fact, only the process as claimed in the invention makes it possible to obtain lutetium diphthalocyanine unambiguously.

We claim:

1. Process for the preparation of lanthanide or yttrium diphthalocyanine, in which:
    (a) a mixture of pure and dehydrated lanthanide or yttrium derivative and phthalonitrile is heated, the reaction temperature being kept below the critical temperature of endothermicity, then
    (b) when an exothermicity appears, the temperature is kept at a temperature below the decomposition temperature of the reactants,
    (c) the reaction product is washed with methanol and dimethylformamide, and
    (d) the lanthanide or yttrium diphthalocyanine obtained is recovered.

2. Process as claimed in claim 1, in which the lanthanide or yttrium derivative is an acetate.

3. Process as claimed in claim 2, wherein lutetium acetate is used, the critical temperature of endothermicity is 305° C. and the decomposition temperature of the reactants is 320° C.

4. Process as claimed in one of claims 1 to 3, in which the molar ratio of the lanthanide or yttrium derivative to phthalonitrile is between 1/6 and 1/12.

5. Process as claimed in claim 1, in which the reaction is carried out under a stream of inert gas, with continuous stirring.

6. Process as claimed in claim 5, in which the gas stream is a stream of argon.

7. Process as claimed in claim 1, in which the reaction is carried out at atmospheric pressure.

8. Process as claimed in claim 1, in which the reaction is carried out in solid phase.

* * * * *

UNITED STATES PATENT AND TRADEMARK OFFICE
CERTIFICATE OF CORRECTION

PATENT NO. : 4,649,195
DATED : March 10, 1987
INVENTOR(S) : Clarisse et al.

It is certified that error appears in the above-identified patent and that said Letters Patent is hereby corrected as shown below:

| COLUMN | LINE | DESCRIPTION |
|--------|------|-------------|
| 1 | 46 | Please delete "tne" and insert --the--. |
| 2 | 55 | Please delete "tnis" and insert --this--. |

Signed and Sealed this

Fifteenth Day of December, 1987

Attest:

DONALD J. QUIGG

*Attesting Officer*     *Commissioner of Patents and Trademarks*